US007878654B2

(12) United States Patent
Mattioli et al.

(10) Patent No.: US 7,878,654 B2
(45) Date of Patent: Feb. 1, 2011

(54) MULTI-PURPOSE OPHTHALMOLOGICAL APPARATUS

(75) Inventors: Renzo Mattioli, Rome (IT); Stefano Frondizi, Rome (IT)

(73) Assignee: Optikon 2000 S.p.A., Rome (IT)

( * ) Notice: Subject to any disclaimer, the term of this patent is extended or adjusted under 35 U.S.C. 154(b) by 38 days.

(21) Appl. No.: 12/061,116

(22) Filed: Apr. 2, 2008

(65) Prior Publication Data

US 2009/0046250 A1 Feb. 19, 2009

(30) Foreign Application Priority Data

Apr. 3, 2007 (IT) .......................... RM2007A0183

(51) Int. Cl.
*A61B 3/10* (2006.01)
(52) U.S. Cl. ...................................... 351/211; 351/212
(58) Field of Classification Search ................ 351/211, 351/212, 237–239
See application file for complete search history.

(56) References Cited

U.S. PATENT DOCUMENTS

| | | | |
|---|---|---|---|
| 3,598,478 A | | 8/1971 | Townsley |
| 3,824,005 A | * | 7/1974 | Woestman .................. 351/211 |
| 4,315,672 A | * | 2/1982 | Muller et al. ............... 351/212 |
| 4,772,115 A | | 9/1988 | Gersten et al. |
| 4,863,260 A | * | 9/1989 | Gersten et al. ............. 351/212 |
| 5,258,791 A | | 11/1993 | Penney et al. |
| 5,341,180 A | | 8/1994 | Isogai et al. |
| 5,500,697 A | * | 3/1996 | Fujieda ...................... 351/212 |
| 5,526,073 A | | 6/1996 | Mattioli |
| 5,873,832 A | | 2/1999 | Maloney et al. |
| 6,050,687 A | | 4/2000 | Bille et al. |
| 6,234,631 B1 | | 5/2001 | Sarver et al. |
| 6,273,566 B1 | | 8/2001 | Kobayashi et al. |
| 6,286,958 B1 | | 9/2001 | Koest |
| 6,409,345 B1 | | 6/2002 | Molebny et al. |
| 6,634,752 B2 | | 10/2003 | Curatu |
| 6,655,805 B2 | | 12/2003 | Fujieda |
| 6,905,209 B2 | | 6/2005 | Mihashi et al. |
| 7,034,949 B2 | | 4/2006 | Horwitz |
| 2005/0018136 A1 | * | 1/2005 | Hayashi ...................... 351/212 |
| 2005/0185143 A1 | * | 8/2005 | Bossche et al. ............... 353/31 |

OTHER PUBLICATIONS

Gullstrand A. "Photographic-ophthalmometric and clinical investigations of corneal refraction" Am J Optom Arch Am Acad Option 1966; vol. 43: pp. 143-214.

(Continued)

*Primary Examiner*—Jordan M. Schwartz
(74) *Attorney, Agent, or Firm*—Roberts Mlotkowski Safran & Cole P.C.

(57) ABSTRACT

The present invention relates to a multi-purpose ophthalmological apparatus, comprising first optical means, provided with one or more first mires, and sensing means for acquiring along a first optical path an image comprising said one or more first mires reflected by a patient's eye, characterised in that it comprises separating optical means for separating the first optical path from at least one second optical path, and in that it further comprises second optical means, provided with one or more second mires, located along the first optical path between the separating optical means and the sensing means, whereby said image further comprises said one or more second mires reflected by the patient's eye.

18 Claims, 6 Drawing Sheets

OTHER PUBLICATIONS

Mattioli R. & Tripoli N.: "Corneal Geometry Reconstruction with the Keratron Videokeratographer", Optom Vis Sci 1997, vol. 74, pp. 881-894.

Klein SA.: "A corneal topography algorithm that produces continuous curvature", Optom Vis Sci 1002;69: 829-834, 1992.

Cohen KL, Tripoli NK, Holmgren DE, Coggins JM: "Assessment of the power and height of radial aspheres reported by a computer-assisted keratoscope" Am J Ophthalmol 1995; vol. 119: pp. 723-732.

Liang J, Grimm B, Goelz S, and Bille JF, "Objective measurement of wave aberrations of the human eye with the use of a Hartmann-Shack wave-front sensor", Journal of the Optical Society of America A 11, 1949-1957, 1994.

Thibos LN, Faao P, Hong M Xin, "Clinical applications of the Shack-Hartmann aberrometer", Optometry and Vision Science vol. 76, pp. 817-825, 1999.

Tripoli NK, Cohen KL, Holmgren DE, Coggins JM: "Assessment of radial aspheres by the Keratron keratoscope using an arc-step algorithm" Am J Ophthalmol 1995; vol. 120: pp. 658-664.

Dekking, H. M., "On the Photography of the Surface of the Cornea", Graefes Archive of Ophthalmology, 1930, vol. 124.

\* cited by examiner

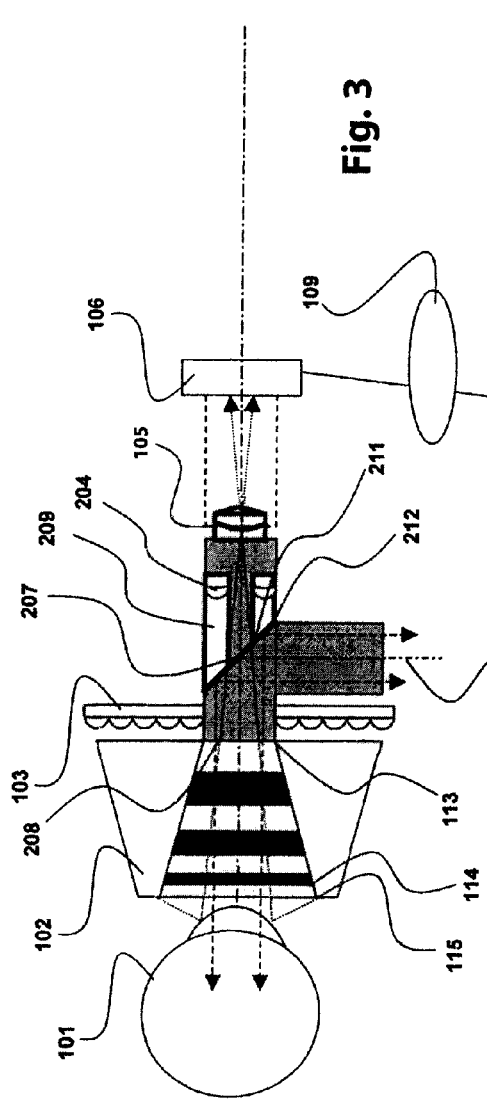
Fig. 3
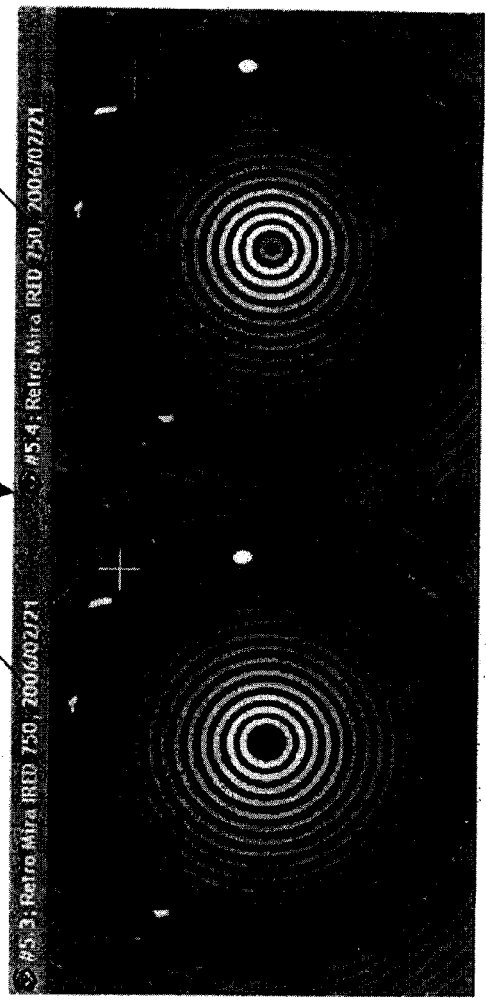
Fig. 3-A  Fig. 3-B

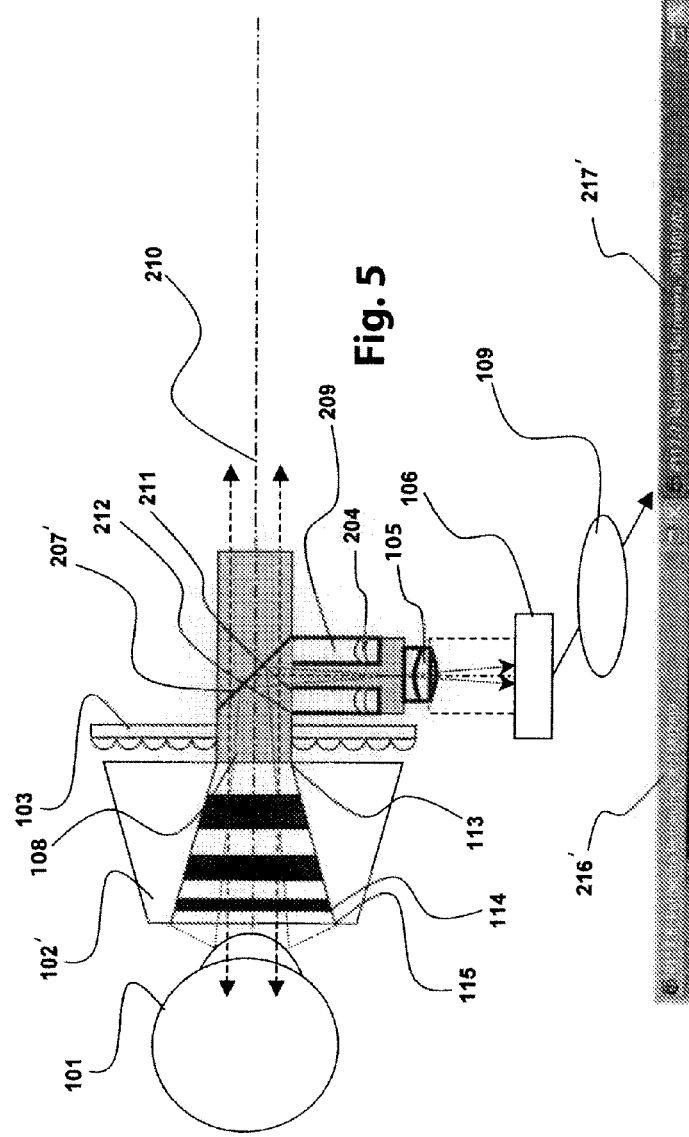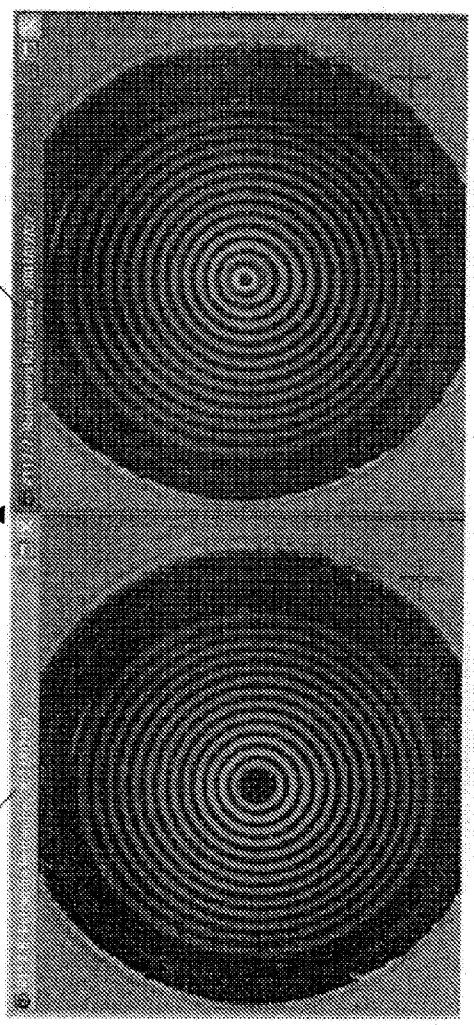
Fig. 5
Fig. 5 -A
Fig. 5 -B

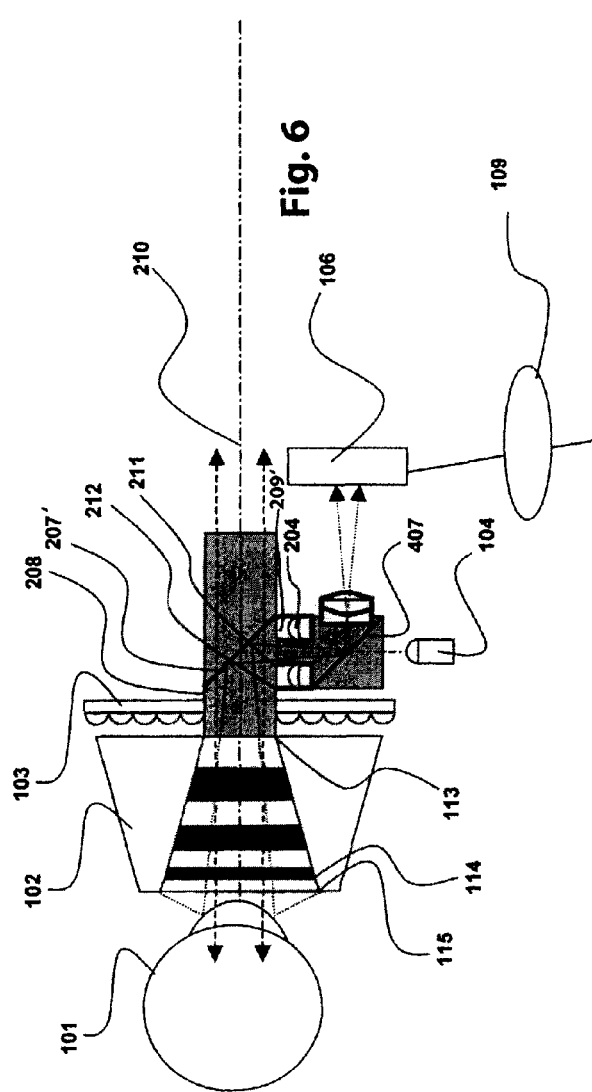
Fig. 6
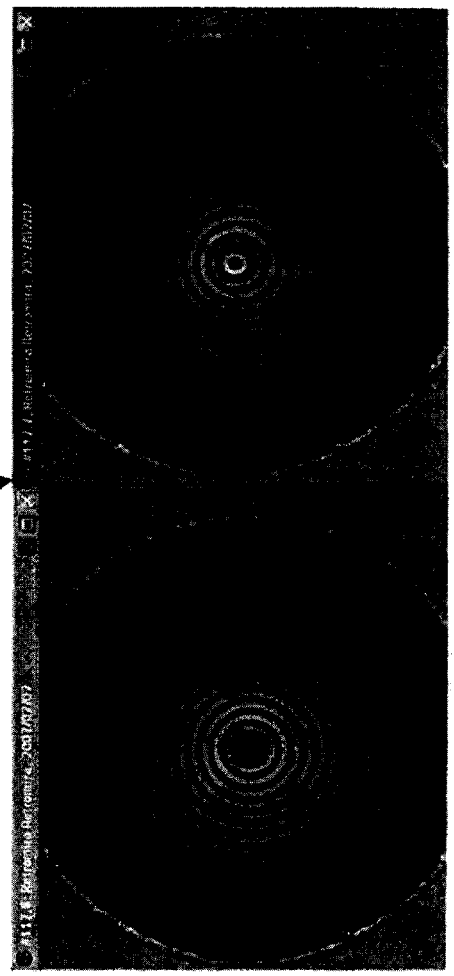
Fig. 6-A  Fig. 6-B

MULTI-PURPOSE OPHTHALMOLOGICAL APPARATUS

CROSS REFERENCE TO RELATED APPLICATIONS

This Application claims priority from Italian Application No. RM2007A000183 filed on Apr. 3, 2007, which is hereby incorporated by reference in its entirety into this Application.

FIELD OF THE INVENTION

The present invention relates to an multi-purpose opthalmological apparatus allowing, in a simple, reliable, precise, and inexpensive way, to measure reflection corneal topography of the human eye along with one or more other opthalmological measurements such as, for instance, the corneal thickness measurement with Scheimpflug camera, the autorefractometry, or the aberrometry (wavefront aberration measurement) through measurement of the retinal reflex and the pupillometry with multi-level brightness.

BACKGROUND OF THE INVENTION

The reflection corneal topography (commonly called as "Placido" one) is a technique for measuring shape and curvatures of the human eye which stems from the Javal and Schiotz opthalmometer of 1889, from the studies of 1896 by Gullstrand (see Gullstrand A.: "Photographic-opthalmometric and clinical Investigations of corneal refraction", *Am J Optom Arch Am Acad Optom* 1966; 43: 143-214), from the disk with concentric rings of 1880 by the Portuguese ophthalmologist Antonio Placido and "cone" embodiments thereof, starting from the Dekking one (see Dekking H M: "Zur Photographie der Hornhautoberflaeche", *Graefes Arch Ophtalmol* 1930; 124:708-30) up to the subsequent developments (such as those disclosed, e.g., in U.S. Pat. No. 3,598,478 to Townsley and U.S. Pat. No. 4,772,115 to Gersten). Thanks to its size and outer shape, such ring cone allows to get closer to the eye, covering with the reflections of its mires, arranged on an inner reflecting or back-illuminated surface, almost the whole cornea, even though at the cost of a higher position sensitivity. In this regard, U.S. Pat. No. 5,526,073 to Mattioli comprises techniques for solving such criticality by acquiring the videokeratography (i.e. the photograph of the mires reflected on the cornea) at a precise distance from the corneal apex.

With reference to FIG. 1, the arrangement of the optical parts of a typical computerised reflection topography unit may be observed with a Placido back-illuminated mires cone. In particular, FIG. 1 schematically shows a Keratron® topography unit from Optikon 2000 S.p.A. company (that is simplified in the mires number), but it should be understood that other conventional reflection topography units, with Placido cone or disk having different shape, type, colour and arrangement of the mires, have in any case equivalent optical arrangements.

The mires cone 102 of transparent material back-illuminated by an illuminator 103, e.g. with surface mount LEDs, has mires marked on its inner surface (having shape of a frustum of cone in the embodiment of FIG. 1) which are constituted by axially symmetrical stripes alternatively black and white, starting from the central hole 108 of the cone 102 that appears black to the patient whose corneal topography of the eye 101 is measured. The image of these mires, reflected on the patient's eye 101 placed at reference distance from the cone 102, appears to the sensor 106 (e.g. a CCD or other sensitive element), through the lens 105, as a pattern of concentric alternatively black and white rings reflected on the cornea, for instance represented by the videokeratography 116 shown in FIG. 1-A (for the sake of simplicity, mires represented in the cone 102 are only a portion of those actually present, as shown by the image 116). Such image taken by the sensor 106, acquired and stored in an area of memory 109 of the computer with which the topography unit is provided, may be shown to the operator on a display. The computer may hence process the image 116 marking the mires and the pupil border, obtaining the image 117 shown in FIG. 1-B, and hence maps 118 representative of the same corneal geometry shown in FIG. 1-C. In this example the ectasia due to a keratoconus is shown by the left lower zone of the images 116 and 117, wherein the rings are close to each other, and of the image 118 where a high instant curvature, typically represented by an area 119 (conventionally in orange-red colours), is measured.

Mires may be arranged in a manner that may be defined as "homogeneous", with a process graphically illustrated in FIG. 2, i.e. causing the image of the black-white and white-black borders to be angularly equally spaced in the photograph of the configuration (or pattern) reflected on a reference spherical surface (usually 43D, mean central curvature of a normal human eye, i.e. R=7.85 mm, since, according to the Javal convention, 1 Dioptre is equal to 337.5/R, where R is the axial or instant curvature radius in mm).

In other words, on the reference spherical surface, the radius of the image of the black-white border 111 of the first white mire, as well as the radial distance between such image and the image of the white-black border 112 of the second mire, between the latter and the image of the black-white border 113, and so on up to the distance between the image of the borders 114 and 115 (i.e. the thickness of the last reflected white ring), are all equal to each other.

FIG. 2 shows how mires (which in this example consist in 8 alternatively black-white white-black borders) may be marked in a homogeneous manner, after having determined: a) the number "n" of such mires; b) the angle "α" by which it is desired that each one of them is spaced from the preceding one in their image reflected on the reference sphere; c) the distance between the corneal apex 120 and the optical centre 121 of the lens 105 and d) the shape and position of the surface provided with such mires (preferably a conical frustum surface of revolution of which, in this example, we take the generatrix 122 as reference). In the sectional view of FIG. 2, the "reflected rays" from the sphere are marked backwards, starting from the optical centre 121 of the lens 105, at angles multiple of "α" with respect to the cone axis, until the same reference sphere is intersected. Hence, still backwards, the respective "impinging ray", symmetrical to the reflected one with respect to the sphere perpendicular radius through the same point, is marked from each one of such intersection points. The "impinging rays" have increasing angles, respectively $\beta_0, \beta_1, \ldots \beta_n$, with respect to the cone axis. Finally the ideal positions of the mires are determined, from the intersection of said impinging rays with the generatrix 122 of the same surface.

However, it is actually possible to choose the angle "α" and the conical surface generatrix in such a manner that the position of the last mire "n" corresponds to a cone mouth of predetermined diameter and at predetermined distance from the eye.

The advantages deriving from a disposition homogeneous arrangement of this kind are known (see Mattioli R. & Tripoli N.: "Corneal Geometry Reconstruction with the Keratron Videokeratographer", *Optom Vis Sci* 1997, 74, 881-894), especially if it is associated with a reconstruction of the corneal geometry with "arc-step" algorithms (see Klein SA.: "A corneal topography algorithm that produces continuous curvature", *Optom Vis Sci* 1002; 69: 829-834; Tripoli N K, Cohen K L, Holmgren D E, Coggins J M: "Assessment of radial aspheres by the Keratron keratoscope using an arc-step algorithm" *Am J Opthalmol* 1995; 120: 658-664) which analyse the whole sequence of mires starting from the apex, with respect to "spherical approximation" algorithms which analyse them one by one (Cohen K L, Tripoli N K, Holmgren D E, Coggins J M: "Assessment of the power and height of radial aspheres reported by a computer-assisted keratoscope" *Am J Opthalmol* 1995; 119: 723-732). Actually, it is not mandatory that the arrangement is strictly homogeneous, e.g. many topography units adopt a central hole 108 wider than the just described one, but this reduces the central space resolution of the map processing and the whole precision.

Instead of the alternatively black-white and white-black circular borders, thin luminous or dark lines may be also used as mires, as commonly adopted by several topography units. However, under equal number of mires of this type the measurement of the maximum curvature that the sensor 106 is capable to detect before they mingle with each other is about half of that obtainable with alternating borders.

As shown in FIG. 1, a mirror 107 with a partially reflecting face, or a "beam-splitter" cube, reflecting the image produced by the assembly 104 for fixation of the patient, may be placed along the optical path between the hole 108 and the lens 105. Such image is generally a luminous point or picture focused at long distance by an optical system not shown in FIG. 1.

A need currently present in the field of measuring opthalmological is the possibility of combining other opthalmological measurements with the corneal topography. In particular, first of all among such measurements there is the ocular aberrometry (or wavefront analysis) having an increasing importance in the opthalmology field. Ocular aberrometry may be measured through several techniques: Laser ray-tracing (e.g. described in U.S. Pat. No. 6,409,345), Tscherning, SRR (Spatially Resolved Refractometer, e.g. described in U.S. Pat. No. 5,258,791), Talbot (e.g. described in U.S. Pat. No. 7,034,949) or the most diffused Shack-Hartmann or S/H technique (see Liang J, Grimm B, Goelz S, and Bille J F, "Objective measurement of wave aberrations of the human eye with the use of a Hartmann-Shack wave-front sensor", Journal of the Optical Society of America A 11, 1949-1957, 1994; Thibos L N, Faao P, Hong M Xin, "Clinical applications of the Shack-Hartmann aberrometer", Optometry and Vision Science 76, 817-825, 1999). All these techniques, apart from SRR, substantially consist in projecting one or more laser beams into the eye and observing their projection on the retina, or collecting and projecting the emerging wavefront on a sensor measuring the distortions thereof. Radiation projected into the eye is in the near infrared, typically ranging from $\lambda$=780 and $\lambda$=940 nm, for both obtaining a good retinal reflex with low energy and not inducing involuntary pupil constriction, which would negatively affect such measurement.

Considering that the ocular aberrometry is often used in the same application context as the corneal topography, integrating corneal topography and aberrometry in only one instrument would offer the advantage of a better alignment between the two measurements. In particular, the photograph of the eye in the two conditions, under dilated pupil in aberrometry and under constricted pupil in photopic conditions, is extremely useful for centring the "eye-tracking" devices during, e.g., laser treatments. In clinical practice and in measurement for making customised contact lenses these complementary double information, topography and aberrometry, allows to foresee the ideal shape of a customised contact lens in both rear and front faces. Alignment and simultaneousity of the two measurements play a fundamental role even in the above.

Several methods have been adopted or proposed for combining reflection topography with an aberrometer.

In most cases, as for instance in the case of the equipments Nidek OPD-scan and Topcon KR-9000PW and of the U.S. Pat. No. 6,655,805 to Fujeda and U.S. Pat. No. 6,905,209 to Mihashi, the unavoidable compromise concerning the central hole of the Placido disk that has to be reasonably large and close to the eye for allowing aberrometry is accepted, compelling to give up a good coverage of the reflected mires within the central area of the topography.

If otherwise it is desired to keep a homogeneous arrangement of the mires as in topography units Keratron® the hole 108 would unavoidably limit the functions of aberrometry, or any other type of measurement combined with topography requiring a wide and close visibility of patient's eye.

By way of example, considering the topography units Keratron® with a 28 mires cone, cone mouth equal to 30 mm of diameter at a distance equal to 1 mm from the eye (i.e. from the reference position of the corneal apex), an eye-cone bottom distance equal to 63.13 mm, an eye-camera lens 105 distance equal to 100 mm and a homogeneous arrangement of the mires as described with reference to FIG. 2, the hole 108 has a diameter of 5.85 mm, definitely smaller than the pupil that is desired to measure with the aberrometry (up to 8 mm). It is possible to have a hole 108 slightly wider (keeping the homogeneity and the number of the mires) by increasing the cone depth, or vice versa, but this would further increase the distance of the aberrometer from the eye, thus reducing the related range of measurable emmetropia.

Other solutions have been proposed for combining in only one apparatus measurements of corneal topography and aberrometry. U.S. Pat. No. 6,234,631 to Sarver (and following ones to the same inventor) has proposed to employ multiple cameras, combining the aberrometry with the measurement of some corneal thicknesses in a reflection topography unit, wherein the Placido disk is made with a suitable chessboard pattern. However, such solution makes cornea reconstruction particularly complex and noisy and videokeratography not much familiar to the medical operator.

Other completely different solutions have been proposed in U.S. Pat. No. 6,050,687 to Bille and U.S. Pat. No. 6,634,752 to Curatu for combining corneal topography with aberrometry, but these, similarly to the solution proposed in U.S. Pat. No. 5,873,832 to Maloney, suffer from the drawback of being rather complex and are not an effective reflection topography since they provide the projection of a wavefront and/or of circular mires onto the eye through optical relays.

Another opthalmological measurement that could be profitably combined with reflection 1a reflection topography is the measurement of the corneal thicknesses with Scheimpflug camera, e.g. proposed in U.S. Pat. No. 5,341,180 to Isogai and U.S. Pat. No. 6,286,958 to Koest, wherein a thin slit light blade is projected perpendicularly to the cornea, at several axis angles, and the thus produced images in radial sections of the same cornea are observed by a camera in oblique position.

Other opthalmological measurements which would be advantageously combined with reflection topography are numerous. Such measurements comprise, by way of example and not by way of limitation, autorefractometry (e.g. proposed in U.S. Pat. No. 5,500,697 to Fujeda) and direct measurement of PSF (Point Spread function) of the eye (e.g. proposed in U.S. Pat. No. 6,273,566 to Kobayashi).

SUMMARY OF THE INVENTION

It is therefore an object of the present invention to provide a multi-purpose opthalmological apparatus allowing, in a simple, reliable, precise, and inexpensive way, to measure reflection corneal topography of the human eye along with one or more other opthalmological measurements, the apparatus overcoming the limitations described above, i.e. solving the compromise between the need of having a central mire being narrow and/or far from the central corneal coverage of the topography and that of having optics being rather wide and close to the eye as required by the other opthalmological measuring techniques. Such opthalmological measurements may comprise, by way of example and not by way of limitation, the aberrometry (wavefront aberration measurement) through measurement of the retinal reflex, the corneal thickness measurement with Scheimpflug camera, the autorefractometry, and the pupillometry with multi-level brightness.

It is specific subject matter of the present invention a multi-purpose opthalmological apparatus, opthalmological apparatus, comprising first optical means, provided with one or more first mires, and sensing means for acquiring along a first optical path an image comprising said one or more first mires reflected by a patient's eye, characterised in that it comprises separating optical means for separating the first optical path from at least one second optical path, and in that it further comprises second optical means, provided with one or more second mires, located along the first optical path between the separating optical means and the sensing means, whereby said image further comprises said one or more second mires reflected by the patient's eye.

Always according to the invention, said separating optical means may comprise at least one interferential optical filter capable to transmit at least one first band of light frequencies and to reflect at least one second band of light frequencies.

Still according to the invention, said separating optical means may comprise at least one filter-mirror and/or at least one beam-splitter cube, the surfaces of which are preferably at least partially anti-reflective.

Furthermore according to the invention, the apparatus may further comprise electronic means for storing said image and performing a reflection corneal topography on the basis of said image.

Always according to the invention, the apparatus may further comprise along said at least one second optical path optical and/or electronic means for performing a measurement of ocular aberrometry, preferably through a measurement of the wavefront coming from the retinal reflex of a beam projected onto the same eye, and/or a measurement of sections of anterior ocular segment through slit light and/or a corneal thickness measurement, preferably with Scheimpflug camera, and/or a measurement of autorefractometry and/or a measurement of PSF (Point Spread function) on the retina and/or a measurement of endothelial microscopy and/or a measurement of corneal confocal and/or a measurement of OCT on the anterior ocular segment or on the retina and/or a measurement of opthalmoscopy and/or a measurement of crystalline opacity density and/or a measurement of perimetry and/or a measurement of micro-perimetry and/or a measurement of the FDT (Frequency doubling) and/or a subjective measurement of glare and/or a measurement of contrast and/or a measurement of visus (vision) and/or a measurement of sensitivity to colours and/or a measurement of pupillometry, preferably with a plurality of luminosity levels, and/or a measurement of pupil in relation to the apex and/or a measurement of iris and/or a measurement of scieral veins and/or a measurement of marking signs, in photopic and/or scotopic-mesopic conditions.

Still according to the invention, the apparatus may comprise along a second optical path an assembly for fixation and/or for controlling the accomodation (fogging) of the patient's eye.

Furthermore according to the invention, said first optical means may comprise at least one illuminator capable to illuminate at least one Placido disk, with plane and/or conical and/or curved surface, and/or at least one Dekking cone, with internal revolution, preferably cylindrical frustum and/or conical frustum, surface.

Always according to the invention, said one or more first mires may comprise alternatively white-black stripes and/or narrow lines and/or alternatively coloured lines and/or alternatively coloured stripes and/or concentric rings and/or cobweb and/or chessboard rings.

Still according to the invention, said second optical means may comprise lighting elements capable to enable a projection of said one or more second mires.

Furthermore according to the invention, said second optical means may comprise a, preferably cylindrical ring, body having a luminous surface and/or a back-illuminated scattering surface.

Always according to the invention, said one or more second mires may comprise alternatively white-black stripes and/or narrow lines and/or alternatively coloured stripes and/or alternatively coloured lines and/or concentric rings and/or cobweb and/or chessboard rings.

Still according to the invention, the sensing means may comprise at least one lens and at least one optoelectronic sensor, preferably of CCD and/or CMOS type.

Furthermore according to the invention, the sensing means may be capable to perform centring and/or monitoring functions.

BRIEF DESCRIPTION OF THE DRAWINGS

The present invention will now be described, by way of illustration and not by way of limitation, according to its preferred embodiments, by particularly referring to the Figures of the enclosed drawings, in which:

FIG. 3 schematically shows a top view of the architecture of a first embodiment of the multi-purpose opthalmological apparatus according to the invention, while FIGS. 3-A and 3-B show two images obtainable with such apparatus;

FIG. 5 schematically shows a top view of the architecture of a second embodiment of the multi-purpose opthalmological apparatus according to the invention, while FIGS. 5-A and 5-B show two images obtainable with such apparatus; and FIG. 6 schematically shows a top view of the architecture of a third embodiment of the multi-purpose opthalmological apparatus according to the invention, while FIGS. 6-A and 6-B show two images obtainable with such apparatus.

In the Figures, alike elements are indicated by same reference numbers.

DETAILED DESCRIPTION

The present invention implements a multi-purpose opthalmological apparatus that combines a reflection topography unit with at least one further opthalmological measurement, the apparatus being capable to generate a reflected mires pattern that is substantially equivalent to those described above with reference to the reflection topography units of the prior art, but with an aperture more suitable for said at least one combined further opthalmological measurement. This is obtained by substantially placing some mires of the Placido cone or disk, hereinafter also referred to as "back-mires", after the point of separation between the optical path used for topography and the one used for the complementary measurement, so as to allow for the latter the use of wider optics closer to the eye.

In the following of the description, reference will be made to embodiments of the multi-purpose opthalmological apparatus which combine the reflection corneal topography with the aberrometry (wavefront aberration measurement) through measurement of retinal reflex. However, it should be understood that other embodiments of the multi-purpose opthalmological apparatus may combine the reflection corneal topography with more than one further opthalmological measurement, and that the further opthalmological measurements are not limited to the aberrometry, but they can comprise other measurements, such as, by way of example and not by way of limitation, the corneal thickness measurement with Scheimpflug camera, the autorefractometry, and the pupillometry with multi-level brightness.

Figure 1:
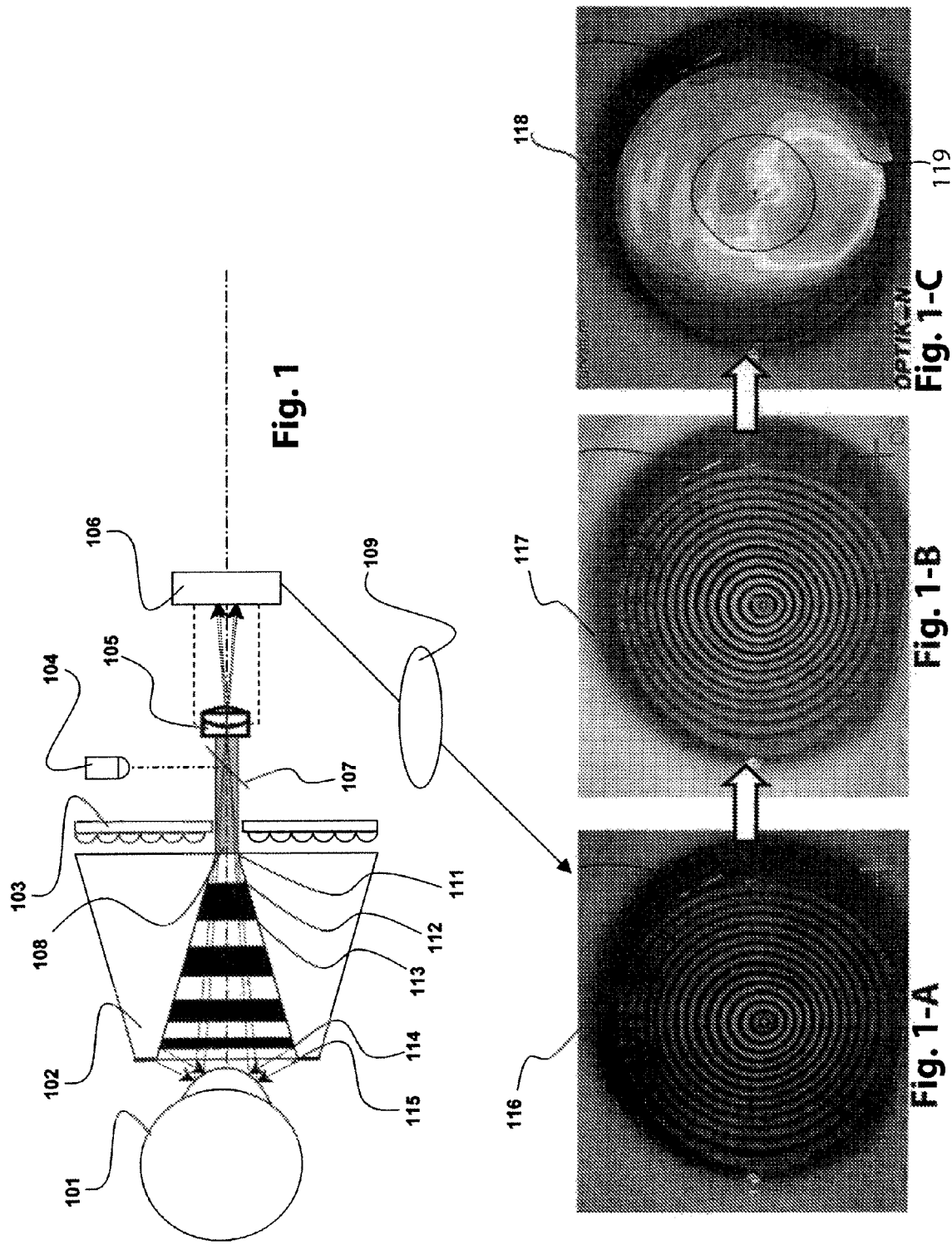
FIG. 1 schematically shows a side or top view of the architecture of a reflection topography unit of the prior art, while FIGS. 1-A, 1-B, and 1-C show three images obtainable with such topography unit.

With reference to FIG. 3, a first embodiment of the multi-purpose opthalmological apparatus may be observed, wherein the mires cone 102' has been shortened with respect to the one of FIG. 1 for creating a wider optical channel through the bottom of the same cone. The more inner mires have been moved behind a filter-mirror 207 and in contact with it in order not to create glare for the camera at its back, that comprises a lens 105 and a sensor 106 (e.g. a CCD). In this regard, the structural arrangement of FIG. 3 is not essential and could be modified in such a way that a side view of the apparatus is similar to the view of FIG. 3.

In particular, the mires cone 102' has been shortened with respect to the one of FIG. 1 by removing at least one pair of mires from the bottom of the cone 102 and keeping the homogeneous arrangement of all the remaining mires. In this way, taking for instance the geometrical data of the Keratron® described above, by eliminating only one pair of white-black mires, the diameter of the hole 108' passes from 5.85 mm to 12.87 mm and its distance from the eye passes from 63.13 mm to 45.06 mm. A filter-mirror 207 is placed behind the mires cone 102' and its illuminator 103. The front face of such mirror 207 is treated as band-pass interferential optical filter designed so as to transmit the light frequencies which must be seen by the camera assembly 105 and 106 and to reflect those necessary to the complementary measurement along the path 210.

A ring cylindrical body 209 containing lighting elements 204 and light scattering elements (not shown) is placed behind the mirror 207, preferably in contact with it for minimising any reflection or back-scattering which could cause glare for the sensor 106, which body has such a suitable shape and size that the effect in the reflections of its borders 211 and 212 onto the reference spherical surface reference (i.e. the patient's eye 101) is substantially equivalent to that of the borders 111 and 112 of the mires "removed" from the cone 102 of the conventional topography unit of FIG. 1.

FIGS. 3-A and 3-B show the videokeratographic images 216 and 217 of the patterns of such configuration which are reflected onto the reference sphere (the patient's eye 101), respectively with lighting 204 on and off.

Figure 2:
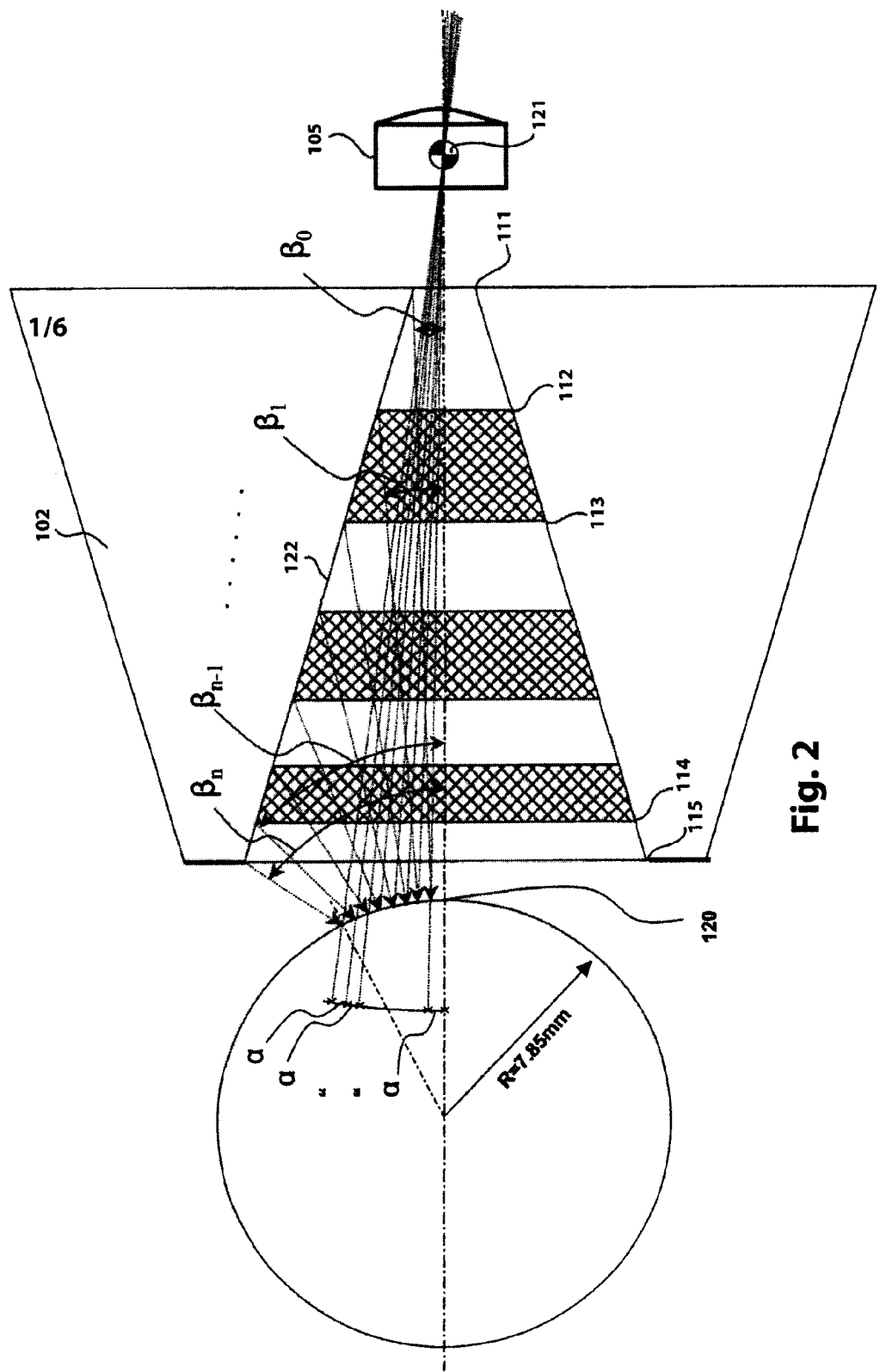
FIG. 2 schematically shows how to mark a homogeneous arrangement of alternatively coloured mires.
Figure 4:
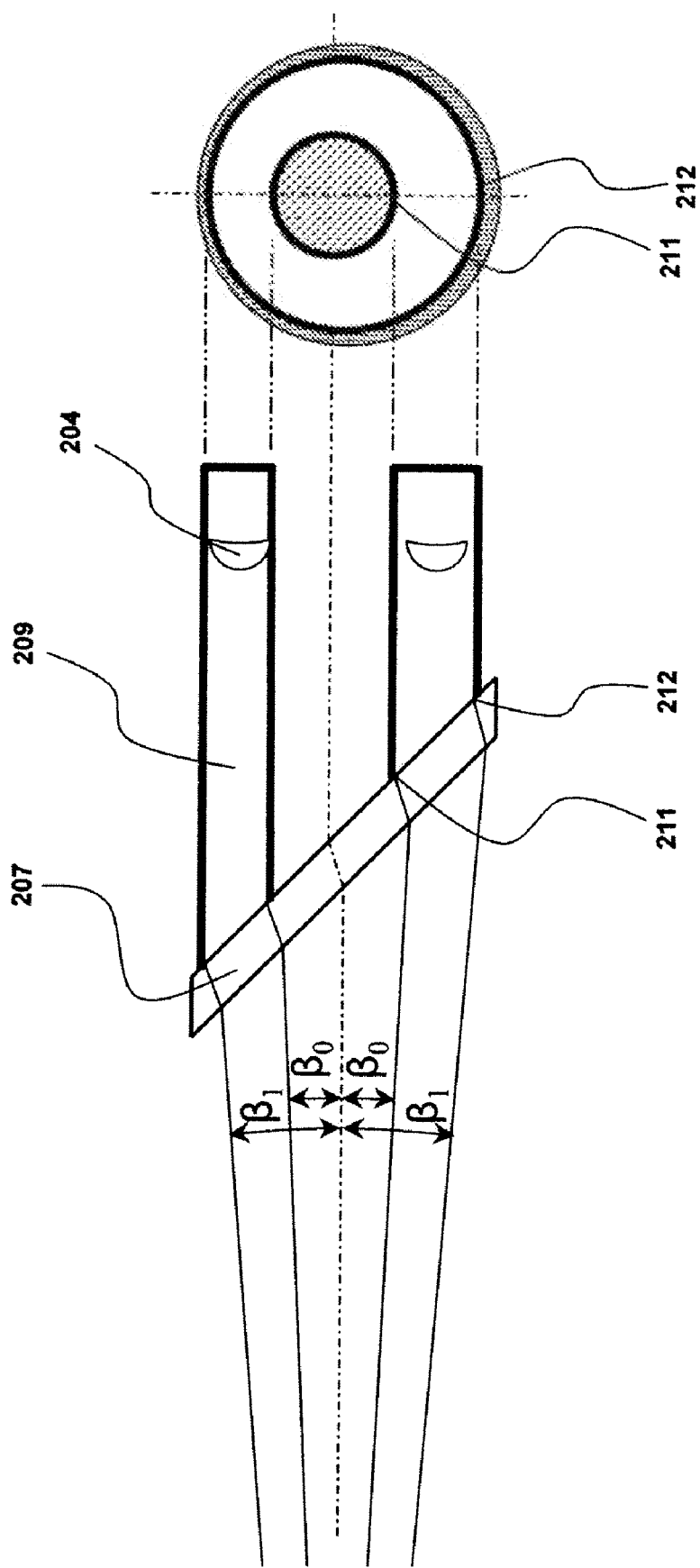
FIG. 4 schematically shows how to track, keeping their homogeneous arrangement, some alternatively coloured mires of an element of the apparatus of FIG. 3.

In particular, in order to keep the homogeneous arrangement of the mires along with the other mires of the Placido cone 102' (or disk), it is necessary that the borders 211 and 212 of the body 209 are seen by the eye under a same angle in every radial direction $\beta_0$, $\beta_1$, . . . shown in FIG. 2. FIG. 4 graphically shows how the reciprocal positions of the back-mires borders 211 and 212 with respect to the visual axis of the camera have to be calculated with the embodiment of FIG. 3, i.e. by marking in the space or in every section plane the "impinging rays" of the process shown in FIG. 2 until meeting the same borders, taking account of the slope of the oblique cut of the body 209, of the thickness of the filter 207 and of the Snell's law.

Alternatively, the body 209 may be axially symmetrical and these mis-centrings may be entrusted to a suitable mask placed behind the same mirror 207, or they may be simply accepted and compensated by computerised processing of the arc-step algorithms and/or by the calibration procedures.

Still alternatively the mirror 207 may be replaced with a beam-splitter cube the surfaces of which are treated with adequate anti-reflection coating.

Other embodiments of the apparatus according to the invention may have a different arrangement of the two (or more) optical paths, where this is also advantageous for carrying out further specific opthalmological measurements.

FIG. 5 shows a second embodiment of the apparatus according to the invention wherein the camera assembly 105 and 106 and the axis of the optical path 210 are reversed with respect to the apparatus of FIG. 3. In this regard, even in this case the structural arrangement of FIG. 5 is not essential and it could be modified in such a way that a side view of the apparatus is similar to the view of FIG. 5. The filter 207' has transfer and reflection functions reversed with respect to the filter 207 of FIG. 3. In this way, all the points of the borders 211 and 212 of the back-mires implemented through a body 209' (which is axially symmetrical, since the asymmetries shown in FIG. 4 due to the oblique base are not present in this case) are equidistant from the eye 101 and there is a lower risk of secondary reflections along the apparatus section dedicated to the topography. In particular, in order to be correctly seen by the operator, the image detected by the sensor 106 requires a mirror reversal in direction (horizontal or vertical depending on how it is arranged), that may be carried out by the computer (not shown) on the image acquired and stored in the memory 109 through turnover in direction, horizontal or vertical depending on how it is arranged. FIGS. 5-A and 5-B show the videokeratographic images 216' and 217' of the patterns of such configuration which are reflected onto the reference sphere (the patient's eye 101), respectively with lighting 204 on and off.

FIG. 6 shows a third embodiment of the apparatus according to the invention wherein, with respect to the apparatus of FIG. 5, a mirror 407 has been added which solves the problem of the reversal of the acquired image. Moreover, where partially transmitting or suitably filtering, the mirror 407 may allow the insertion of a further measurement parallel to the topography and to that of the optical path 210, or the insertion behind it of an assembly 104 for the fixation of the patient's eye 101, or an assembly for controlling the accomodation (fogging) in combination with or alternatively to it. Also in this case, the structural arrangement of FIG. 6 is not essential and could be modified in such a way that a side view of the apparatus is similar to the view of FIG. 6. FIGS. 6-A and 6-B show the videokeratographic images 216' and 217' of the patterns of such configuration which are reflected onto the reference sphere (the patient's eye 101), respectively with lighting 204 on and off.

It is useful to point out that in all the embodiments of the multi-purpose opthalmological apparatus according to the invention described so far or in any case implementable the camera assembly 105 and 106 is conveniently usable by the operator for centring and (more or less automatically) monitoring the patient's eye 101 during the parallel measurement (aberrometry or other), should it be either simultaneous or sequential to the reflection corneal topography. In fact, such a centring and monitoring function is necessary in all previously assumed or the combinations thereof. To this end, it is necessary and sufficient that the illuminator 103 and/or the illuminator 204 have frequencies visible to the sensor 106 and transmitted by the filter 207 of FIG. 2 (or 207' of FIGS. 5 and 6). For reducing possible disturbances, such source could be also turned off at the instant of acquisition of the measurements through the channel 210.

By way of example and not by way of limitation, if the further combined opthalmological measurement is a Shack-Hartman aberrometry employing a super-luminescent diode having wavelength λ equal to 840-870 nm as light source, the filter 207 of FIG. 3 could be of high-pass type (while the filter 207' of FIGS. 5 and 6 could be of low-pass type) with cut-off frequency of about the wavelength λ equal to 800 nm, and the illuminators 103 and 204 could contain LED with wavelength λ equal to 730-750 nm. At this wavelength the human eye is not much sensitive and hence the little amount of radiating energy necessary to the CCD (or CMOS) sensors usable in the sensor 106 does not induce significant pupil constriction. The same illuminators 103 and 204 may contain visible frequency LED for photopic lighting. In this way, simultaneously to the two sequential measurements of aberrometry and corneal topography, pupillometry measurements in conditions of scotopic and photopic lighting and acquisition of the respective images usable for the "eye-tracking" devices are obtained.

Also the control of positioning of the corneal apex at the reference distance necessary to the topography, such as for instance the one described in U.S. Pat. No. 5,526,073 to Mattioli, may be profitably exploited in said at least one further opthalmological measurement combined with the topography.

The preferred embodiments have been above described and some modifications of this invention have been suggested, but it should be understood that those skilled in the art can make other variations and changes, without so departing from the related scope of protection, as defined by the attached claims.

The invention claimed is:

1. A multi-purpose ophthalmological apparatus, comprising a first optical means, provided with one or more first mires, and sensing means for acquiring along a first optical path an image comprising said one or more first mires reflected by a patient's eye, the apparatus further comprising separating optical means for separating the first optical path from at least one second optical path, and a second optical means, provided with one or more second mires, located along the first optical path between the separating optical means and the sensing means, whereby said image further comprises said one or more second mires reflected by the patient's eye, and wherein said one or more first mires and said one or more second mires are homogeneously arranged.

2. An apparatus according to claim 1, wherein said separating optical means comprises at least one interferential optical filter capable to transmit at least one first band of light frequencies and to reflect at least one second band of light frequencies.

3. An apparatus according to claim 1, wherein said separating optical means comprises at least one filter-mirror and/or at least one beam-splitter cube.

4. An apparatus according to claim 1, wherein it further comprises electronic means for storing said image and performing a reflection corneal topography on the basis of said image.

5. An apparatus according to claim 1, wherein it further comprises along said at least one second optical path optical and/or electronic means for performing a measurement of ocular aberrometry, through a measurement of the wavefront coming from the retinal reflex of a beam projected onto the same eye, and/or a measurement of sections of anterior ocular segment through slit light and/or a corneal thickness measurement, with Scheimpflug camera, and/or a measurement of autorefractometry and/or a measurement of PSF (Point Spread function) on the retina and/or a measurement of endothelial microscopy and/or a measurement of corneal confocal and/or a measurement of OCT on the anterior ocular segment or on the retina and/or a measurement of ophthalmoscopy and/or a measurement of crystalline opacity density and/or a measurement of perimetry and/or a measurement of micro-perimetry and/or a measurement of the FDT (Frequency doubling) and/or a subjective measurement of glare and/or a measurement of contrast and/or a measurement of vision and/or a measurement of sensitivity to colours and/or a measurement of pupillometry, with a plurality of luminosity levels, and/or a measurement of pupil in relation to the apex and/or a measurement of iris and/or a measurement of scleral veins and/or a measurement of marking signs, in photopic and/or scotopic-mesopic conditions.

6. An apparatus according to claim 1, wherein it comprises along said at least one second optical path an assembly for fixation and/or for controlling fogging of the patient's eye.

7. An apparatus according to claim 1, wherein said first optical means comprises at least one illuminator capable to illuminate at least one Placido disk, with plane and/or conical and/or curved surface, and/or at least one Dekking cone, with internal revolution, cylindrical frustum and/or conical frustum surface.

8. An apparatus according to claim 1, wherein said one or more first mires comprises alternatively white-black stripes and/or narrow lines and/or alternatively coloured lines and/or alternatively coloured stripes and/or concentric rings and/or cobweb and/or chessboard rings.

9. An apparatus according to claim 1, wherein said second optical means comprises lighting elements capable to enable a projection of said one or more second mires.

10. An apparatus according to claim 9, wherein said second optical means comprises a body having a luminous surface and/or a back-illuminated scattering surface.

11. An apparatus according to claim 10, wherein said one or more second mires comprises alternatively white-black stripes and/or narrow lines and/or alternatively coloured stripes and/or alternatively coloured lines and/or concentric rings and/or cobweb and/or chessboard rings.

12. An apparatus according to claim 1, wherein the sensing means comprises at least one lens and at least one optoelectronic sensor.

13. An apparatus according to claim 1, wherein the sensing means perform centring and/or monitoring functions.

14. An apparatus according to claim 10, wherein said ring is a cylindrical ring.

15. An apparatus according to claim 12, wherein the at least one optoelectronic sensor comprises a sensor of CCD and/or CMOS type.

16. An apparatus according to claim 3, wherein the surfaces of said at least one filter-mirror and/or said at least one beam-splitter cube are at least partially anti-reflective.

17. An apparatus according to claim 10, wherein said body is a cylindrical ring or annular body.

18. An apparatus according to claim 1, wherein the sensing means comprises one lens.

* * * * *